United States Patent
Czygan et al.

(10) Patent No.: US 8,521,282 B2
(45) Date of Patent: Aug. 27, 2013

(54) IMPLANTABLE MEDICAL SYSTEM WITH ACOUSTIC SENSOR TO MEASURE MITRAL BLOOD FLOW

(75) Inventors: Gerald Czygan, Buckenhof (DE); Michael Lippert, Ansbach (DE); Tibor Nappholz, Evergreen, CO (US)

(73) Assignee: Biotronik CRM Patent AG, Baar (CH)

( * ) Notice: Subject to any disclaimer, the term of this patent is extended or adjusted under 35 U.S.C. 154(b) by 1209 days.

(21) Appl. No.: 11/948,935

(22) Filed: Nov. 30, 2007

(65) Prior Publication Data
US 2008/0146934 A1    Jun. 19, 2008

(30) Foreign Application Priority Data
Dec. 8, 2006  (EP) ..................................... 06025401

(51) Int. Cl.
*A61N 1/365*    (2006.01)
(52) U.S. Cl.
USPC ............... 607/17; 607/24; 600/439; 600/465; 600/468; 600/526
(58) Field of Classification Search
USPC ............. 607/9, 17, 18, 24, 26, 119; 600/439, 600/454, 462, 467, 468, 465, 526
See application file for complete search history.

(56) References Cited

U.S. PATENT DOCUMENTS

| | | | |
|---|---|---|---|
| 5,139,020 A | | 8/1992 | Koestner et al. |
| 5,156,154 A | | 10/1992 | Valenta, Jr. et al. |
| 5,156,157 A | | 10/1992 | Valenta, Jr. et al. |
| 5,183,040 A | | 2/1993 | Nappholz et al. |
| 5,188,106 A | | 2/1993 | Nappholz et al. |
| 5,243,976 A | | 9/1993 | Ferek-Petric et al. |
| 5,316,001 A | | 5/1994 | Ferek-Petric et al. |
| 5,325,860 A | * | 7/1994 | Seward et al. ................ 600/468 |
| 5,334,222 A | | 8/1994 | Salo et al. |
| 5,409,009 A | | 4/1995 | Olson |
| 5,535,751 A | * | 7/1996 | Raz ................................ 600/459 |
| 5,544,656 A | | 8/1996 | Pitsillides et al. |
| 5,584,868 A | * | 12/1996 | Salo et al. ........................ 607/17 |
| 5,795,298 A | * | 8/1998 | Vesely et al. ................... 600/450 |
| 5,876,345 A | * | 3/1999 | Eaton et al. .................... 600/466 |

(Continued)

FOREIGN PATENT DOCUMENTS
EP    1 410 756    4/2004

OTHER PUBLICATIONS
European Search Report, dated Mar. 19, 2007.

*Primary Examiner* — Carl H Layno
*Assistant Examiner* — Eugene Wu
(74) *Attorney, Agent, or Firm* — Arc IP Law, PC; Joseph J. Mayo (57) ABSTRACT

A heart stimulation system comprises an electrode lead comprising at least one stimulation electrode a stimulation pulse generator adapted to generate electric stimulation pulses and being connected to said electrode lead for delivering electric stimulation pulses to at least one chamber of a heart via said stimulation electrode, and a control unit that is connected to said stimulation pulse generator. The electrode lead is a coronary sinus lead adapted to be placed inside the coronary sinus of a human heart and comprises an ultrasonic transducer that is adapted to measure a velocity of blood flow across a mitral valve of a human heart and that is placed on said coronary sinus lead such that the ultrasonic transducer is placed in the coronary sinus or the great cardiac vein when the coronary sinus lead is in its implanted state.

19 Claims, 6 Drawing Sheets

(56) References Cited

U.S. PATENT DOCUMENTS

| | | |
|---|---|---|
| 6,298,269 B1 | 10/2001 | Sweeney |
| 6,398,734 B1 | 6/2002 | Cimochowski et al. |
| 6,421,565 B1 | 7/2002 | Hemmingsson |
| 6,740,076 B2 | 5/2004 | Hoben et al. |
| 6,757,563 B2 | 6/2004 | Sweeney |
| 6,795,732 B2 | 9/2004 | Stadler et al. |
| 6,970,742 B2 | 11/2005 | Mann et al. |
| 7,037,266 B2 | 5/2006 | Ferek-Petric et al. |
| 2003/0023296 A1 | 1/2003 | Osypka |
| 2003/0083702 A1 | 5/2003 | Stadler et al. |
| 2003/0195496 A1* | 10/2003 | Maguire et al. .............. 606/27 |
| 2003/0199936 A1* | 10/2003 | Struble et al. ............... 607/25 |
| 2003/0204140 A1* | 10/2003 | Ferek-Patric et al. ........ 600/439 |
| 2004/0176688 A1* | 9/2004 | Haldeman .................. 600/443 |
| 2004/0176810 A1 | 9/2004 | Stadler |
| 2005/0027323 A1 | 2/2005 | Mulligan |
| 2006/0100668 A1 | 5/2006 | Ben-David et al. |
| 2010/0125210 A1* | 5/2010 | Hastings et al. ............. 600/462 |

* cited by examiner

IMPLANTABLE MEDICAL SYSTEM WITH ACOUSTIC SENSOR TO MEASURE MITRAL BLOOD FLOW

This application takes priority from European Patent Application EP 06025401.8, filed 8 Dec. 2006, the specification of which is hereby incorporated herein by reference.

BACKGROUND OF THE INVENTION

1. Field of the Invention

The invention refers to an implantable medical system for treating a heart. In particular, the invention refers to an implantable heart stimulation system comprising an implantable heart stimulator such as an implantable pacemaker and/or an implantable cardioverter/defibrillator (ICD) and an electrode arrangement connected to the heart stimulator.

2. Description of the Related Art

Implantable heart stimulators can be used for treating a variety of heart disorders like bradycardia, tachycardia or fibrillation by way of electric stimulation pulses delivered to the heart tissue, the myocardium. Strong enough a stimulation pulse outside a heart chamber's refractory period leads to excitation of the myocardium of that heart chamber, which in turn is followed by a contraction of the respective heart chamber.

Depending on the disorder to be treated, such heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of its distal end. A stimulation pulse also is called a pace. Similarly, pacing a heart chamber means stimulating a heart chamber by delivery of a stimulation pulse.

In order to be able to sense a contraction of a heart chamber, that naturally occurs without artificial stimulation and that is called intrinsic, the heart stimulator usually comprises at least one sensing stage that is connected to a sensing electrode on said electrode placed in the heart chamber. An intrinsic excitation of a heart chamber results in characteristic electrical potentials that can be picked up via the sensing electrode and that can be evaluated by the sensing stage in order to determine whether an intrinsic excitation—called: intrinsic event—has occurred.

Usually, a heart stimulator features separate stimulation generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event $A_P$ (atrial paced event) or a ventricular stimulation event $V_P$ (ventricular paced event), respectively.

Similarly, common heart stimulators feature separate sensing stages for each heart chamber to be of interest. In a dual chamber pacemaker usually two separate sensing stages, an atrial sensing stage and a ventricular sensing stage, are provided that are capable to detect intrinsic atrial events $A_S$ (atrial sensed event) or intrinsic ventricular events $V_S$ (ventricular sensed event), respectively.

As known in the art, separate sensing and pacing stages are provided for three-chamber (right atrium RA, right ventricle RV, left ventricle LV) or four-chamber (right atrium RA, left atrium LA, right ventricle RV, left ventricle LV) pacemakers or ICDs.

By means of a sensing stage for a heart chamber to be stimulated, the pacemaker is able to only trigger stimulation pulses when needed, that is when no intrinsic excitation of the heart chamber occurs in time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited. Such intrinsic (natural, non-stimulated) excitation are manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms.

In heart cycle, an excitation of the myocardium leads to depolarization of the myocardium that causes a contraction of the heart chamber. If the myocardium is fully depolarized it is unsusceptible for further excitation and thus refractory. Thereafter, the myocardium repolarizes and thus relaxes and the heart chamber is expanding again. In a typical electrogram (EGM) depolarization of the ventricle corresponds to a signal known as "R-wave". The repolarization of the ventricular myocardium coincides with a signal known as "T-wave". Atrial depolarization is manifested by a signal known as "P-wave".

A natural contraction of a heart chamber thus can be detected by evaluating electrical signals sensed by the sensing channels. In the sensed electrical signal the depolarization of an atrium muscle tissue is manifested by occurrence of a P-wave. Similarly, the depolarization of ventricular muscle tissue is manifested by the occurrence of a R-wave. A P-wave or a R-wave thus leads to an atrial sense event As or a ventricular sense event Vs, respectively.

Several modes of operation are available in a state of the art multi mode pacemaker. The pacing modes of a pacemaker, both single and dual or more chamber pacemakers, are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse is delivered to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

A dual chamber pacemaker featuring an atrial and a ventricular sensing stage and an atrial and a ventricular stimulation pulse generator can be operated in a number of stimulation modes like VVI, wherein atrial sense events are ignored and no atrial stimulation pulses are generated, but only ventricular stimulation pulses are delivered in a demand mode, AAI, wherein ventricular sense events are ignored and no ventricular stimulation pulses are generated, but only atrial stimulation pulses are delivered in a demand mode, or DDD, wherein both, atrial and ventricular stimulation pulses are delivered in a demand mode. In such DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

There are few approaches known to directly measure blood flow in the heart or a vessel close to the heart by means of an ultrasound Doppler sensor to be able to better adapt stimulation therapy to the needs of a patient.

Acoustic signals of various kind can be used for monitoring the cardiovascular and respiratory systems. Ultrasound in particular is widely used for both external and internal monitoring of cardiac structures and cardiac dynamics. Echocardiography especially is used extensively in non-invasive diagnosis and in the invasive form as Intra Cardiac Echocardiography (ICE). The standard external instruments are used for structural evaluations and also for dynamic functions such as blood flow and myocardial contractility measurements. Blood flow is usually measured by the Doppler effect and is extensively used in research work with more invasive techniques where catheters carry the ultrasonic crystal.

Echocardiography has become a powerful standard tool in the armamentaria of the cardiologist. It is used for many real time measurements such as blood flow measurement, heart valve timing observations and for many other purposes. These measurements are all performed from outside the body, e.g., by applying an ultrasonic transducer on the skin surface. Recently Intra Cardiac Echocardiography has become very popular. Intra Cardiac Echocardiography is carried out with catheters introduced into the heart. These catheters are highly specialized with some of them rotating at up to 1800 rpm and some having multiple crystals on them allowing full two dimensional cross sectional echo of the heart. This allows the close inspection of all the features of the heart and allow very precise location of catheters into the heart. In research various catheters probes and sensors have been used extensively. These are in the form of catheters with single or multiple crystals allowing such measurements as flow in small arteries and veins, in particular coronary arteries after a stent implant. These measurements are carried out using sonometry (distance measurement), Doppler for flow measurements and 'time of flight' for flow measurements. In sonometry and 'time of flight' measurement two ultrasonic crystals are required. These crystals are spaced apart. With sonometry the spacing needs to be the full span of the distance to be measured and in 'time of flight' the spacing is much shorter as only the influence on the speed of the ultrasound beam is measured.

The ultrasound measurements discussed use a range of frequencies from 1 MHz up to 40 MHz. The range of the measurement tends to dictate the frequency.

Although ultrasound is used extensively in acute measurements chronic measurements in humans have not been done effectively to date. Some chronic work has been done in animals but to a very limited extent. The reason for this is the complexity of the measurement and the power requirements. The complexity of the measurement entails the design of the probe, the positioning of the probe and the processing of the data. Ultrasound at higher frequencies can be made very directional and this is an advantage, but in an implant maintaining precise location over long periods of time is hard to do. In chronic human implants only very simple sensors have been realized and used sparingly. In the field of Pacing and Defibrillation only less than a hundred true sensors have been implanted to date as compared to the implanting of close to 500,000 devices per year.

There are numerous patents teaching the use of ultrasound in implantable devices. These patents range from the use of sonomicrometry to Doppler and in some cases even scavenging total acoustic energy.

The more relevant patents in this area are: U.S. Pat. Nos. 5,139,020; 5,156,154; 5,156,157; 5,183,040; 5,188,106; 5,243,976; 5,316,001; 5,334,222; 5,409,009; 5,544,656; 6,298,269; 6,398,734; 6,421,565; 6,757,563; 6,740,076; 6,795,732; 6,970,742; 7,037,266; US 2003/0083702; US 2003/0204140; US 2004/0176810; US 2005/0027323.

BRIEF SUMMARY OF THE INVENTION

It is an object of the invention to provide an implantable medical device (IMD) providing an efficient sensor for measuring mitral blood flow.

According to the invention, this object is achieved by a heart stimulation system that comprises an electrode lead comprising at least one stimulation electrode a stimulation pulse generator adapted to generate electric stimulation pulses and being connected to said electrode lead for delivering electric stimulation pulses to at least one chamber of a heart via said stimulation electrode, and a control unit that is connected to said stimulation pulse generator.

The electrode lead is a coronary sinus lead (CS lead) adapted to be placed inside the coronary sinus of a human heart. The electrode lead comprises an ultrasonic transducer that is adapted to measure a velocity of blood flow across a mitral valve of a human heart. The ultrasonic transducer is positioned on the CS lead such that it is placed in the coronary sinus or in the great cardiac vein when the CS lead is properly implanted.

Thus, an IMD is formed that includes an ultrasonic transducer that is integrated into a pacing or defibrillation lead of the device.

Preferably, the control unit is connected to said ultrasonic transducer via a ultrasonic transducer control unit that is adapted to generate a flow velocity output signal for the control unit that reflects a flow velocity, and wherein the control unit is adapted to process said flow velocity output signal.

In a preferred embodiment the acoustic transmitter and receiver of the ultrasonic transducer is implemented by a single sensor crystal positioned on the lead. The crystal is preferably excited by a pulse of high frequency electrical energy within a frequency range of 2 MHz-8 MHz. This electrical energy of the high frequency pulse is converted by the crystal into ultrasonic acoustic wave that is emitted and sonifies the blood and shifts the frequency when reflected by the blood. The reflected acoustic wave signal is received by the crystal and transformed in a high frequency electric signal that can be further processed in order to receive a flow velocity signal. The flow velocity signal preferably is derived from a frequency shift between the emitted acoustic wave and the reflected signal that is picked up by the same crystal. Thus, the crystal forms a Doppler sensor.

Preferred embodiments of the ultrasonic transducer and of the lead the transducer is part of, include:

The crystal preferably is a piezoelectric crystal and preferably is placed along the axis of the lead. In a further preferred embodiment, the crystal is integrated into a ring electrode that is placed on said electrode lead.

Preferably, the ultrasonic transducer is adapted in a way that an emitted acoustic wave travels into a direction perpendicular to the electrode lead and the reflected signal is received from that direction, respectively, wherein the ultrasonic transducer is placed on said lead at a position in the coronary sinus that is close to the mitral valve, when the electrode lead is in its implanted state.

Alternatively, the ultrasonic transducer is adapted in a way that an emitted acoustic wave travels into a proximal direction with respect to the electrode lead and the reflected signal is received from that direction, respectively, wherein the ultrasonic transducer is placed on said lead at a position in the great cardiac vein, when the electrode lead is in its implanted state.

The ultrasonic transducer may be adjustable with respect to the direction an emitted acoustic wave travels along.

The piezoelectric crystal may be made from Barium Titanate or Lead Zirconate Titanate. Barium Titanate is preferred as it contains no lead. Alternatively, a piezoelectric polymer can be used.

In another alternative embodiment, the ultrasonic transducer is a capacitive ultrasonic transducer.

Preferably, the piezoelectric crystal or an alternative ultrasonic transducer has lateral dimension that are adapted to the wavelength of an emitted ultrasonic wave such that the emitted ultrasonic wave has an angle of beam spread between 10° and 90°. The spread angle of the beam is controlled by the relationship of the wavelength of the ultrasonic transducer to the dimensions of the ultrasonic transducer. If the ultrasonic transducer is too small the beam pattern is widely spread and consequently the returned energy is greatly diminished.

With respect to integration of the ultrasonic transducer into the electrode lead, it is preferred that the ultrasonic transducer is mounted between a matching layer in the front, a backing layer in the back and an absorbing layer behind the backing layer if viewed from outside the electrode lead.

Preferably, the ultrasonic transducer is connected to the ultrasonic transducer control unit with a coax cable.

With respect to the ultrasound transducer control unit, it is preferred that:

the ultrasonic transducer control unit is adapted to excite the ultrasonic transducer by a pulse of electrical energy within a frequency range of 2 MHz-8 MHz, preferably below 5 MHz.

the ultrasonic transducer control unit is adapted to excite the ultrasonic transducer with a high frequency voltage pulse having a sufficient voltage in the order of e.g. 10 volts (in the case the ultrasonic transducer is a piezoelectric crystal), wherein the high frequency voltage pulse preferably has a pulse duration in the order of 1 to 5 micro-seconds. The pulse duration preferably is shorter than an expected time of flight between emission of said acoustic wave and receiving said reflected signal. Thus, all energy of the high frequency voltage pulse is 'quenched' prior to looking at the reflected signal.

the ultrasonic transducer control unit is adapted to amplify and mix a received signal generated by the ultrasonic transducer when receiving a reflected signal to eliminate a carrier frequency and to generate a Doppler shift signal reflecting a flow velocity. This is, because the electric signal generated by the ultrasonic transducer—in particular if the ultrasonic transducer is a piezoelectric crystal—from the reflected acoustic wave signal is usually in the order of micro volts which then has to be appropriately amplified and mixed to eliminate the carrier and look for the Doppler shift. The signal processing is similar to a radio receiver.

the ultrasonic transducer control unit is adapted to generate high frequency pulses with a duty cycle of 3 to 9 pulses in with a time window of 100 ms to 300 ms duration beginning with a left atrial excitation or contraction, that is, a left atrial event. The flow through the mitral valve is comparatively slow which means the Doppler shift will be small and smeared over the time of the AV delay, usually about 160 ms. As little as 5 pulses are believed to give a good indication of the flow through the mitral valve.

the ultrasonic transducer control unit is adapted to apply a time window for receiving a reflected signal wherein the time window is adapted to an expected time of flight between emission of said acoustic wave (ultrasonic pulse) and receiving said reflected signal in order evaluate only that part of the reflected signal that is reflected by a region of interest, e.g. blood flow through the mitral valve. Thus, interference by other reflected signals reflected from other blood flows e.g. in the coronary artery, can be eliminated. Preferably, the time window for receiving the reflected signal after emitting an ultrasonic pulse is adjustable in order to allow adaptation to a particular position of the ultrasonic transducer after implantation of the electrode lead carrying the transducer.

the ultrasonic transducer control unit is adapted to generate high frequency pulses only within a measurement period of 5 to 10 minutes a day. This further saves energy.

The control unit preferably is adapted to optimize an atrioventricular delay AVD by measuring the mitral blood flow velocity after a left atrial event and triggers a left ventricular stimulation pulse when the flow velocity comes to zero, close to zero, or below a certain threshold value. Preferably the control unit varies the atrioventricular delay AVD for a few beats each and to determines an optimal AVD value. The optimal AVD value preferably is stored in a memory together with the heart rate under which the value was determined. The control unit preferably repeats determination and storing of an optimal AVD value under different metabolic conditions. Preferably, the control unit creates a table in the memory that allocates an optimal AVD value to each heart rate. Preferably, separate tables for different event types, e.g., for atrial paced and sensed events are created. The control unit then is able to trigger right and left ventricular stimulation pulses with an optimal AVD in dependence of the current heart rate due to the table.

Preferably, the control unit is also adapted to determine and monitor a mitral regurgitation (MR) during the systole. In a preferred embodiment, the control unit is adapted to store an amount of mitral backflow during the systole as a diagnostic parameter in the memory. The control unit can be adapted to estimate a MR severity index from the temporal velocity distribution of backflow from the left ventricle into the left atrium. The control unit can further be adapted to estimate a MR severity index from the velocity-time-integral of the mitral reflux.

For the purpose of heart synchronization therapy CRT a heart stimulation system is preferred that comprises stimulation pulse generators for generating right atrial and right ventricular stimulation pulses. In such heart stimulation system, the control unit is adapted to control said cardiac synchronization therapy such that right ventricular stimulation pulses and left ventricular stimulation pulses are triggered with an interventricular delay VVD and wherein a pacing mode is automatically chosen from right ventricular stimulation, left ventricular stimulation or biventricular stimulation and the VVD is automatically adjusted based on the MR measurements. In such embodiment the control unit is adapted to apply different pacing modes from time to time and to chose the pacing mode leading to a minimum of mitral regurgitation. The control unit is further adapted to automatically vary the interventricular delay until an interventricular delay value is found that lead to a minimum of mitral regurgitation.

The control unit can be further adapted to determine a systolic LV pressure gradient based on measurement of mitral regurgitation.

Additionally, the control unit can be adapted to determine a relaxation function of the left ventricle based on measurement of mitral regurgitation. In such embodiment, the control unit is preferably adapted to determine the relaxation function by determining the time period between a ventricular event and the beginning of mitral flow into the LV.

In yet another preferred embodiment, the control unit is adapted to determine a decreased mitral flow velocity during passive filling of the left ventricle before a left atrial contraction.

For patients the benefits of such device is that electrical therapy can be monitored and optimized with sensors that measure true hemodynamic status. Especially the status in the left ventricle, which at this stage is only accessible with ultrasound.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
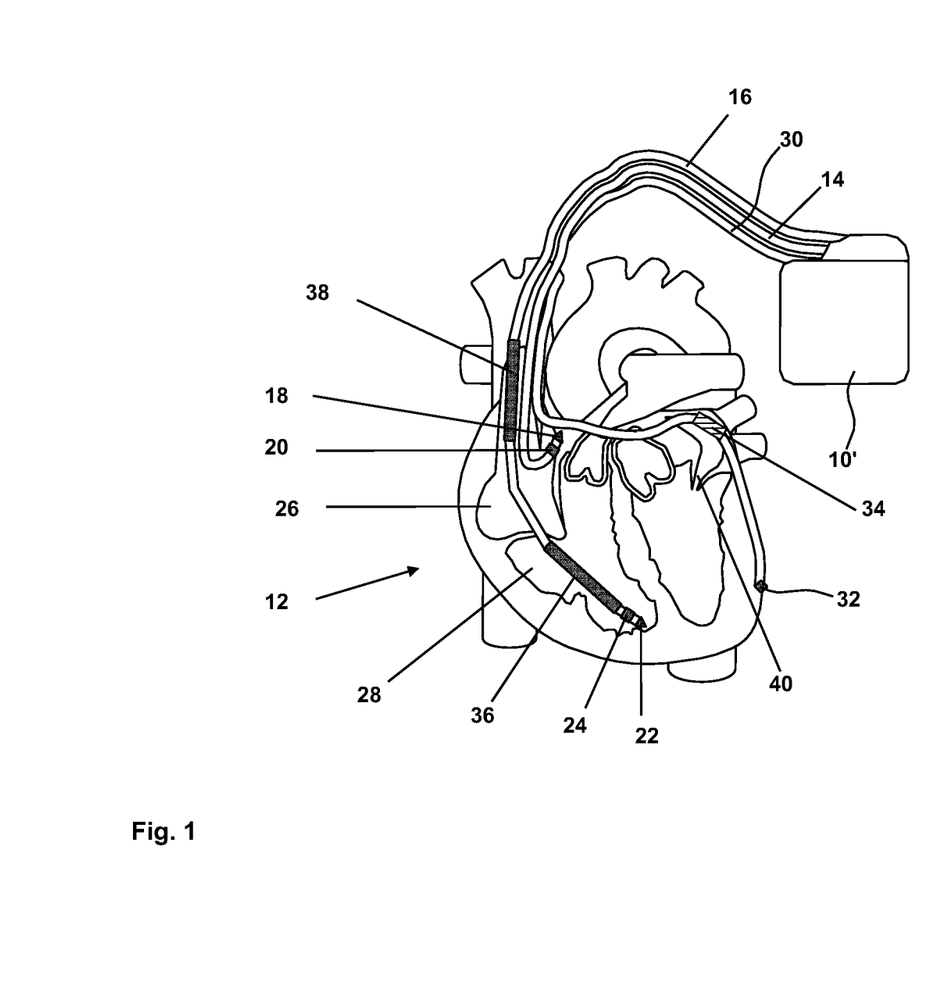
FIG. 1 shows a dual chamber pacemaker connected to leads placed in a heart.

In FIG. 1 a three chamber pacemaker/implantable defibrillator/cardioverter ICD 10 as heart stimulator connected to pacing/sensing leads placed in a heart 12 is illustrated. ICD 10 is electrically coupled to heart 12 by way of leads 14, 16 and 30. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Lead 16 also has a ventricular defibrillation electrode 36 and an vena cava defibrillation electrode 38. Electrodes 18 and 22 are tip-electrodes at the very distal end of leads 14 and 16, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring. Defibrillation electrodes 36 and 38 are helical coil electrodes providing a large surface.

Electrode lead 30 is a coronary sinus electrode lead that provides a left ventricular tip electrode 32 at its very distal end. Furthermore, where electrode lead 30 circumvents mitral valve 40 of heart 12, a Doppler sensor 34 is integrated into electrode lead 30. Doppler sensor 34 comprises a piezo-electric crystal for emitting directed ultrasonic waves and an ultrasound receiver. Such Doppler sensor is generally known in the art.

Figure 2:
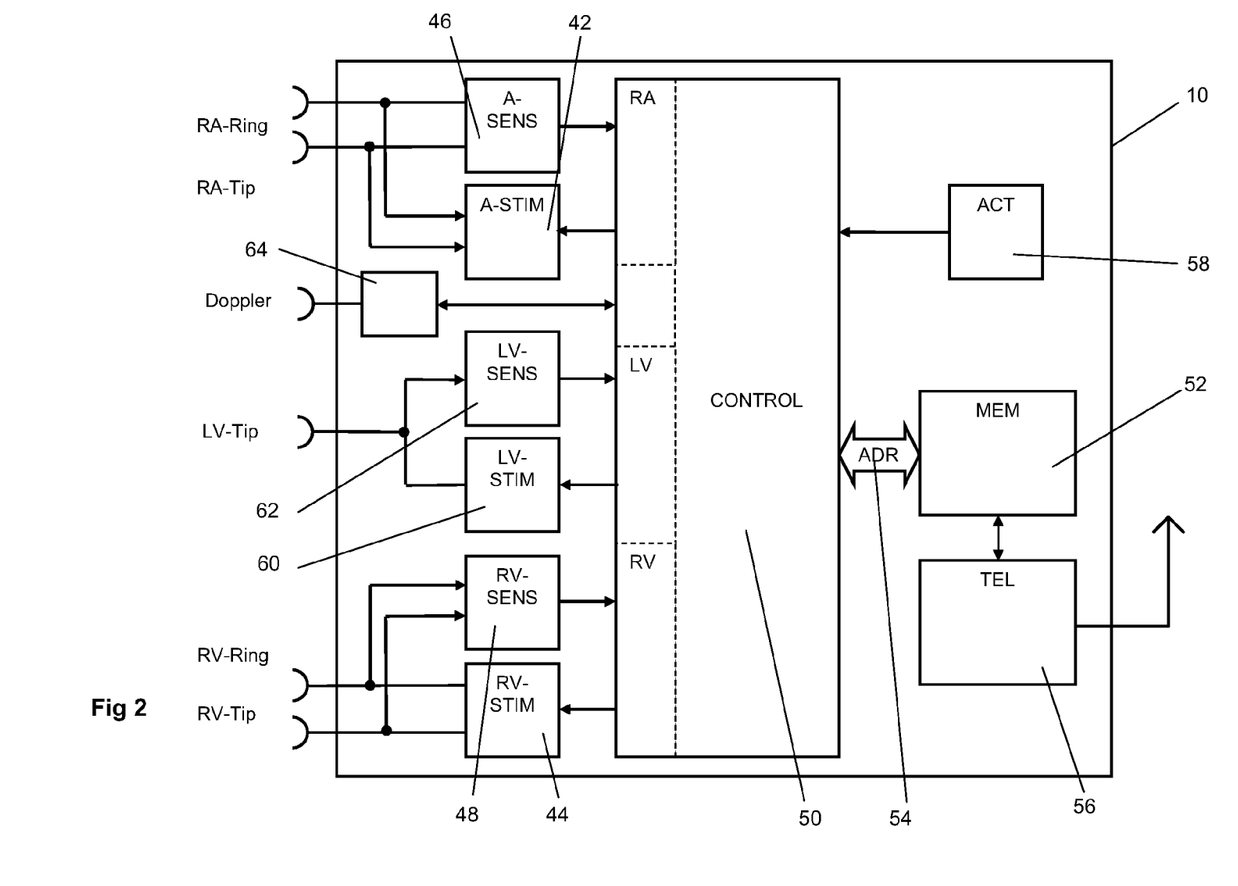
FIG. 2 is a block diagram of an implantable medical device according to the invention.

Referring to FIG. 2 a simplified block diagram of a three chamber pacemaker 10' is illustrated. No defibrillator is illustrated. However, pacemaker 10' could provide added modules for delivery of defibrillation shocks via electrodes 36 and 38 as shown in FIG. 1.

During operation of the pacemaker leads 14, 16 and 30 are connected to respective output/input terminals of pacemaker 10 as indicated in FIG. 1 and carry stimulating pulses to the tip electrodes 18, 22 and 32 from an atrial stimulation pulse generator A-STIM 42, a right ventricular pulse generator RV-STIM 44 and a left ventricular pulse generator LV-STIM 60, respectively. Further, electrical signals from the atrium are carried from the electrode pair 18 and 20, through the lead 14, to the input terminal of an atrial channel sensing stage A-SENS 46; and electrical signals from the right ventricle are carried from the electrode pair 22 and 24, through the lead 16, to the input terminal of a right ventricular sensing stage RV-SENS 48. Electrical signals from the left ventricle are carried from electrode 32, through the lead 30, to the input terminal of a left ventricular sensing stage LV-SENS 62. Doppler sensor 34 is connected to a Doppler sensor control unit 64 via electrode lead 30 as well.

Controlling the dual chamber pacer 10 is a control unit CTRL 50 that is connected to sensing stages A-SENS 46, RV-SENS 48 and LV-SENS 62 and to stimulation pulse generators A-STIM 42, RV-STIM 44 and LV-STIM 60. Control unit CTRL 50 receives the output signals from the atrial sensing stage A-SENS 46 and from the ventricular sensing stages RV-SENS 48 and LV-SENS 62. The output signals of sensing stages A-SENS 46 and RV-SENS 48 are generated each time that a P-wave representing an intrinsic atrial event or an R-wave representing an intrinsic right ventricular event, respectively, is sensed within the heart 12. An As-signal is generated, when the atrial sensing stage A-SENS 46 detects a P-wave and a Vs-signal is generated, when the right ventricular sensing stage V-SENS 48 detects an R-wave.

Control unit CTRL 50 also generates trigger signals that are sent to the atrial stimulation pulse generator A-STIM 42 and the ventricular stimulation pulse generators RV-STIM 44 and LV-STIM 60, respectively. These trigger signals are generated each time that a stimulation pulse is to be generated by the respective pulse generators A-STIM 42, RV-STIM 44 or LV-STIM 60. The atrial trigger signal is referred to simply as the "A-pulse", and the ventricular trigger signals are referred to as the "RV-pulse" or "LV-pulse", respectively. During the time that either an atrial stimulation pulse or ventricular stimulation pulse is being delivered to the heart, the corresponding sensing stage, A-SENS 46 and/or RV-SENS 48 and/or LV-SENS 60, is typically disabled by way of a blanking signal presented to these amplifiers from the control unit CTRL 50, respectively. This blanking action prevents the sensing stages A-SENS 46, RV-SENS 48 and LV-SENS 62 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event $A_{rs}$ but ignored.

Control unit CTRL 50 comprises circuitry for timing ventricular and/or atrial stimulation pulses according to an adequate stimulation rate that can be adapted to a patient's hemodynamic need.

Still referring to FIG. 2, the pacer 10 may also include a memory circuit MEM 52 that is coupled to the control unit CTRL 50 over a suitable data/address bus ADR 54. This memory circuit MEM 52 allows certain control parameters, used by the control unit CTRL 50 in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM 52 for later retrieval and analysis.

A telemetry circuit TEL 56 is further included in the pacemaker 10. This telemetry circuit TEL 56 is connected to the control unit CTRL 50 by way of a suitable command/data bus. Telemetry circuit TEL 56 allows for wireless data exchange between the pacemaker 10 and some remote programming or analyzing device which can be part of a centralized service center serving multiple pacemakers.

The pacemaker 10 in FIG. 1 is referred to as a three chamber pacemaker because it interfaces with the right atrium 26, the right ventricle 28 and the left ventricle of the heart 12. Those portions of the pacemaker 10 that interface with the right atrium, e.g., the lead 14, the P-wave sensing stage A-SENS 46, the atrial stimulation pulse generator A-STIM 42 and corresponding portions of the control unit CTRL 50, are commonly referred to as the atrial channel RA. Similarly, those portions of the pacemaker 10 that interface with the right ventricle 28, e.g., the lead 16, the R-wave sensing stage V-SENS 48, the ventricular stimulation pulse generator V-STIM 44, and corresponding portions of the control unit CTRL 50, are commonly referred to as the right ventricular channel RV. A left ventricular channel includes those portions of the pacemaker 10 that interface with the left ventricle, e.g., the lead 30, the left ventricular sensing stage LV-SENS 62, the left ventricular stimulation pulse generator LV-STIM 60, and corresponding portions LV of the control unit CTRL 50

In order to allow rate adaptive pacing in a DDDR or a DDIR mode, the pacemaker 10 further includes a physiological sensor ACT 58 that is connected to the control unit CTRL 50 of the pacemaker 10. While this sensor ACT 58 is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Figure 3:
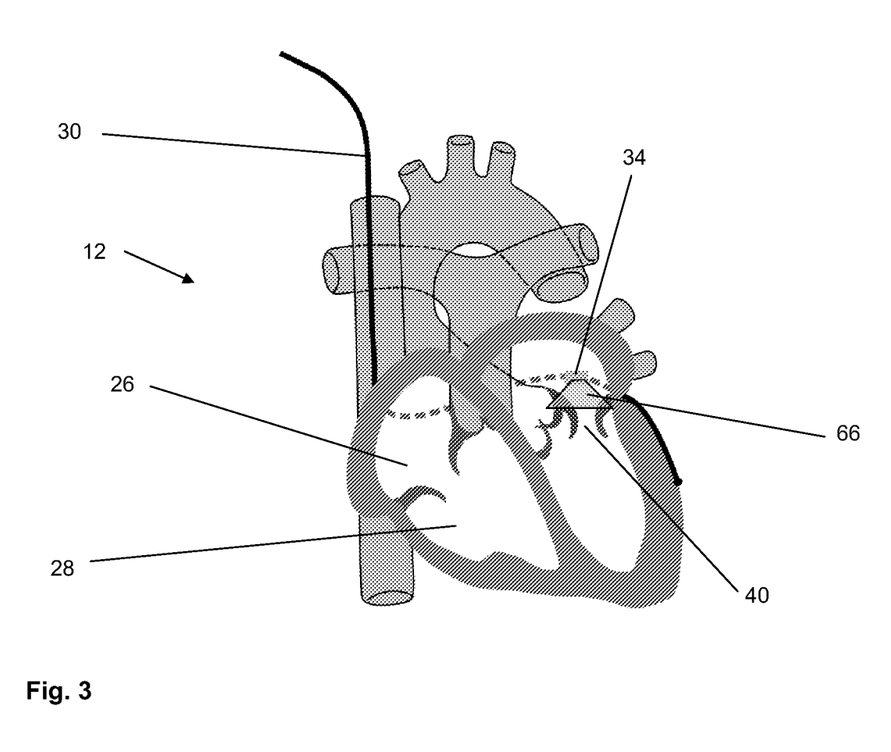
FIG. 3 shows a preferred lead arrangement including an ultrasound Doppler sensor placed in the coronary sinus of a heart.

As pointed out earlier, Doppler sensor 34 is integrated into coronary sinus electrode lead 30. Arrangement of Doppler sensor 34 is such that its ultrasonic transducer is placed on electrode lead 30 at a position in the coronary sinus that is close to the mitral valve 40, when the electrode lead is in its implanted state; see FIG. 3. The ultrasonic transducer is adapted in a way that an emitted acoustic wave 66 travels into a direction perpendicular to the electrode lead 30 and the reflected signal is received from that direction, respectively. The piezoelectric crystal of the ultrasonic transducer has lateral dimensions that are adapted to the wavelength of an emitted ultrasonic wave 66 such that the emitted ultrasonic wave has an angle of beam spread of about 10° to 60°.

Figure 4:
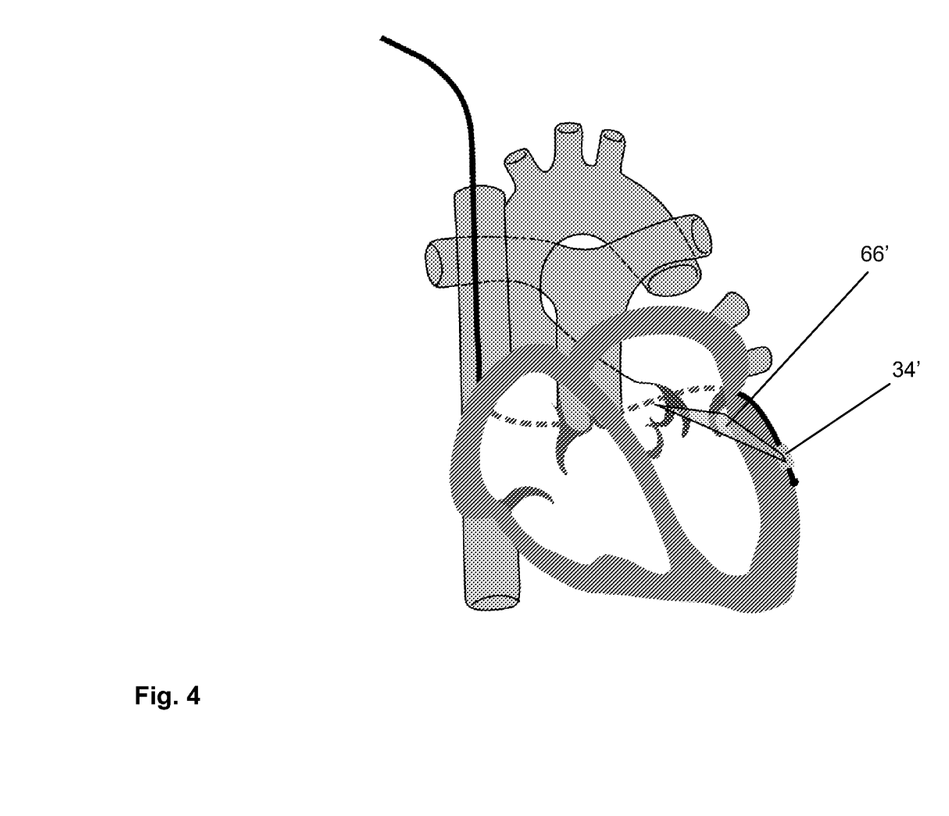
FIG. 4 shows an alternative lead arrangement including an ultrasound Doppler sensor placed in great cardiac vein of a heart.

Alternatively, Doppler sensor 34' can be integrated into coronary sinus electrode lead 30' such that its ultrasonic transducer is placed a position in the great cardiac vein, when the electrode lead is in its implanted state; see FIG. 4. The ultrasonic transducer then is adapted in a way that an emitted acoustic wave 66 travels into a proximal direction with respect to the electrode lead 30' and the reflected acoustic wave signal is received from that direction, respectively. The piezoelectric crystal of the ultrasonic transducer of Doppler sensor 34' has lateral dimensions that are adapted to the wavelength of an emitted ultrasonic wave 66' such that the emitted ultrasonic wave has an angle of beam spread of about 10° to 60°.

Figure 5:
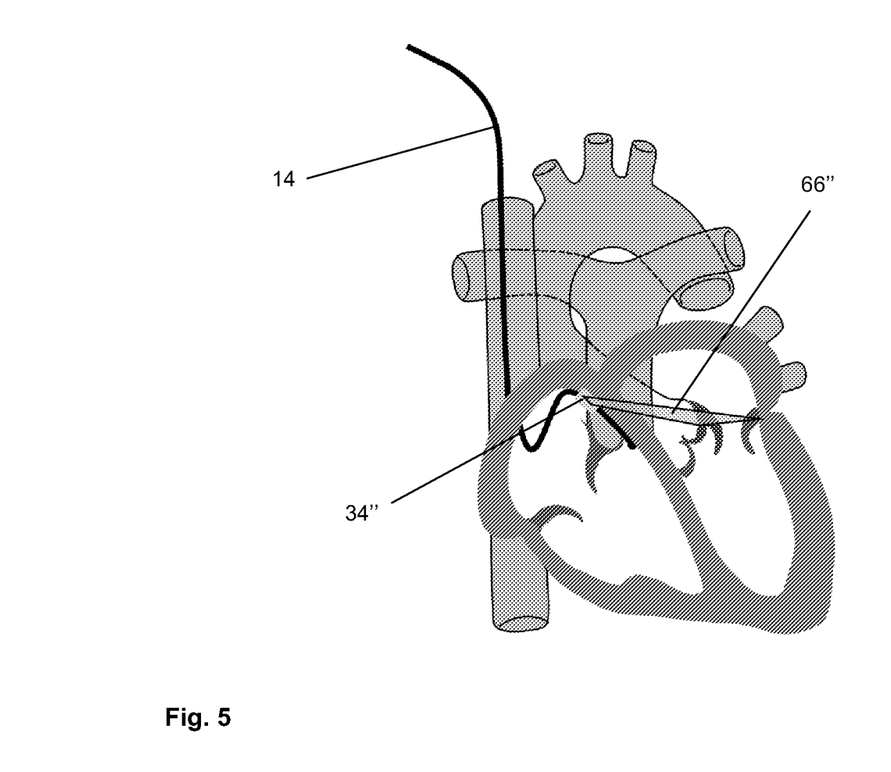
FIG. 5: shows another alternative lead arrangement including an ultrasound Doppler sensor placed in right atrium of a heart.

In another alternative embodiment, Doppler sensor 34' can be part of atrial electrode lead 14 such that Doppler sensor 34" is placed in the right atrium close to the atrial septum; see FIG. 5. Again, the piezoelectric crystal of Doppler sensor 34" is dimensioned such that the emitted ultrasonic wave 66" has an angle of beam spread of about 10° to 60°.

Figure 6:
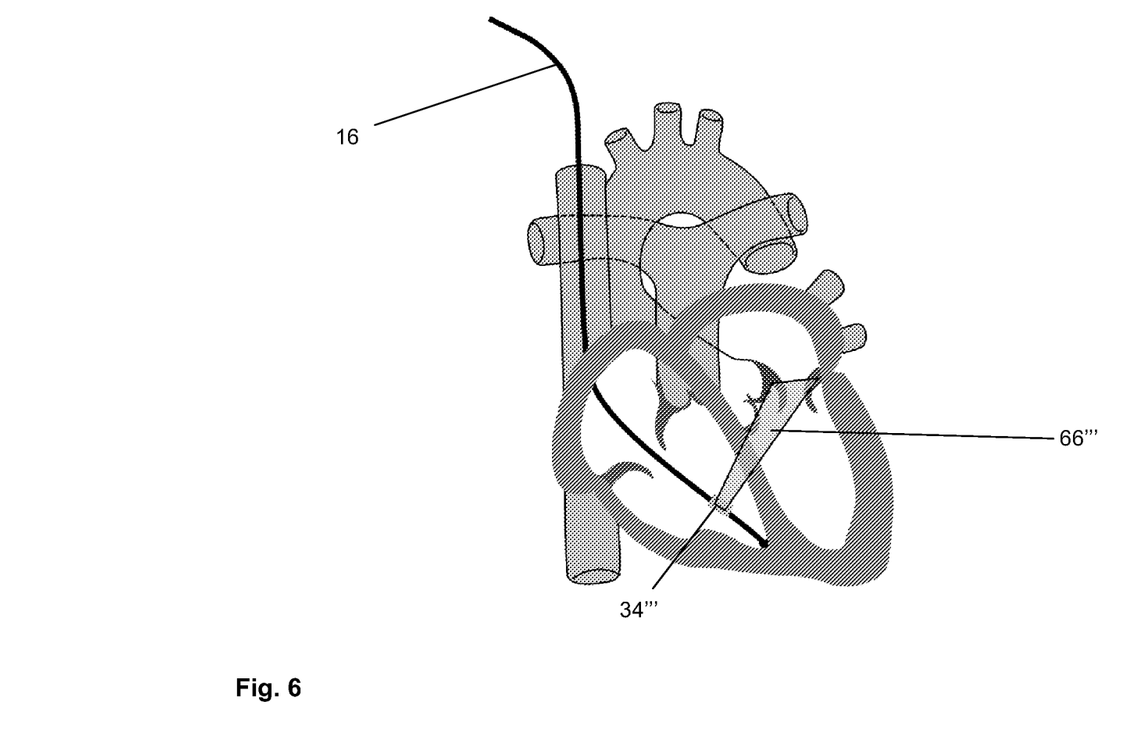
FIG. 6: shows a third alternative lead arrangement including an ultrasound Doppler sensor placed in right ventricle of a heart.

In yet another alternative embodiment, Doppler sensor 34" is part of right ventricular electrode lead 16 such that Doppler sensor 34''' is placed in the right ventricle as shown in FIG. 6. Dimensions of the piezoelectric crystal of Doppler sensor 34''' are such that the emitted ultrasonic wave 66''' has an angle of beam spread of about 10° to 60°.

The acoustic transmitter and receiver of the ultrasonic transducer is implemented by a single sensor crystal positioned on the lead. The crystal is a piezoelectric crystal that is excited by a voltage pulse of high frequency electrical energy within a frequency range of 2 MHz-5 MHz. This electrical energy of the high frequency pulse is converted by the crystal into ultrasonic acoustic wave that is emitted and sonifies the blood and shifts the frequency when reflected by the blood. The reflected acoustic wave signal is received by the crystal and transformed in a high frequency electric signal that can be further processed in order to receive a flow velocity signal. The flow velocity signal preferably is derived from a frequency shift between the emitted acoustic wave and the reflected signal that is picked up by the same crystal. Thus, the piezoelectric crystal together with Doppler sensor control unit 64 form a Doppler sensor, that is connected to control unit CTRL 50 and that forwards a flow velocity signal to control unit 50 when activated.

The piezoelectric crystal preferably is made from Barium Titanate and is connected to Doppler sensor control unit 64 by way of a coax cable in electrode lead 30.

The ultrasonic transducer control unit 64 is adapted to excite the crystal by a high frequency voltage pulse of a frequency of about 5 MHz. The high frequency voltage pulse has a voltage in the order of 10 volts and a pulse duration in the order of 1 to 5 micro-seconds. The pulse duration is shorter than an expected time of flight between emission of said acoustic wave and receiving said reflected signal.

The ultrasonic transducer control unit 64 is adapted to amplify and mix the electric signal generated by the crystal when receiving the reflected ultrasonic acoustic wave signal to eliminate a carrier frequency and to generate a Doppler shift signal reflecting a flow velocity. The Doppler shift signal is the flow velocity signal that is forwarded to control unit CTRL 50 for further processing.

The Doppler sensor formed by the piezoelectric crystal and the ultrasonic transducer control unit 64 is not permanently activated. For one flow velocity measurement, ultrasonic transducer control unit 64 generates high frequency pulses with a duty cycle of 5 pulses in a time window of 100 ms to 300 ms duration beginning with a left atrial excitation or contraction, that is, a left atrial event. Flow velocity measurement is carried out during a measurement period of 5 to 10 minutes a day.

The control unit CTRL 50 is adapted to determine an adequate heart rate or stimulation rate in any manner known as such. The control unit CTRL 50 uses the flow velocity signal received from the Doppler sensor in different ways:

Optimization of the AV-Delay AVD.

The optimal time for the LV stimulation pulse is when the ventricular filling phase is completed. The IMD 10 measures the mitral flow after a LA event (sense or pace) and paces the LV when the flow comes to zero, close to zero, or below a certain threshold value. This enables not only baseline AVD optimization at rest but also optimization under all conditions during daily life. For this dynamic AVD optimization the AVD is varied for a few beats each and the optimal value determined from the flow sensor signal. The so found value is stored in memory MEM 52 of IMD 10 together with the heart rate under which the value was determined. This procedure is repeated under different metabolic conditions, i.e., for different heart rates. The heart rate may be intrinsic or sensor driven. A table in memory MEM 52 is created that allocates an optimal AVD value to each heart rate. Separate tables exist for different event types, e.g., for atrial paced and sensed events. Control unit CTRL 50 of IMD 10 triggers ventricular stimulation pulses with an optimal AVD in dependence of the current heart rate due to the table. The whole procedure may be repeated from time to time to track changed physiologic conditions.

Alternatively, the AV-delay can be optimized based on an evaluation of the mitral stroke volume such that the mitral velocity-time integral VTI is maximized.

Determination and Monitoring of Mitral Regurgitation (MR) During the Systole.

MR e.g. can be caused by a valve insufficiency or by poor synchronization of the ventricles (see below). The amount of mitral backflow during the systole is determined by control unit CTRL 50 and stored/transmitted as a diagnostic parameter. A MR severity index can be estimated. The amount of reversely streaming blood is estimated from the temporal velocity distribution of backflow from the left ventricle into the left atrium, e.g., by the velocity-time-integral VTI of the mitral reflux.

If the IMD includes an additional Doppler sensor for aortic flow measurement, the MR also can be determined from the difference of the mitral SV (estimated from the mitral velocity-time integral VTI) and the aortic SV (estimated from the aortic VTI).

For CHF patients the MR often is increased significantly caused by a poor synchronization of the ventricles and by a dilatation of the left ventricle. IMD 10 optimizes a cardiac resynchronization therapy CRT wherein both ventricles are paced by means of right ventricular stimulation pulse generator 44 and left ventricular stimulation pulse generator 60 such that MR is minimized. The pacing mode (RV stimulation, LV stimulation or BiV stimulation) and the interventricular delay VVD in case of biventricular stimulation are automatically adjusted by control unit CTRL 50 based on the MR measurements by means of the Doppler sensor 34. Control unit switches between different modes of pacing from time to time in order to determine a pacing mode resulting in a minimum MR. If the pacing mode is biventricular stimulation mode wherein both ventricles are pace with a programmable interventricular delay VVD, the VVD is automatically varied till a value with a minimal MR is found. This value is considered to be the best one as the optimal synchronization and the best pumping efficacy of the LV is obtained.

Determination of the Systolic Left Ventricular Pressure Gradient.

The systolic left ventricular pressure gradient can be assessed from the MR measurements, i.e., from the velocity of blood that streams back into the left atrium during the pre ejection period PEP. Under the assumptions that the left atrial pressure change and the change of the blood velocity in the left ventricle are neglectable during the PEP, that the body position does not change during the measurement, and that no friction losses occur, the left ventricular pressure gradient can be estimated from the Bernoulli equation:

$$\frac{dp_{LV}}{dt} \approx \frac{\Delta p_{LV}}{\Delta t} \approx \frac{\rho_{blood}}{2} \frac{v_{LA}^2(t_2) - v_{LA}^2(t_1)}{t_2 - t_1}$$

with $p_{LV}$—LV blood pressure
$v_{LA}$—LA blood velocity
$\rho_{blood}$—blood density.

I.e., the left ventricular pressure gradient is computed by control unit CTRL 50 from two consecutive left atrial velocity measurements during the PEP. The max. dp/dt for instance can be estimated, if several measurements are taken within the PEP. dp/dt_max is a measure for the left ventricular contractility. The relevance of this parameter for several diagnostic and therapeutic options is described elsewhere and needs not to be discussed here. The advantage of this method is, that the left ventricular pressure gradient can be continuously monitored from an implanted electrode lead without the need for a pressure sensor. This method may be combined with other methods, e.g., with the determination of left ventricular volume changes via the intracardiac impedance measurement, which is described elsewhere.

Determination of the Relaxation Function of the Left Ventricle.

From the mitral flow during the early diastolic phase, i.e., the relaxation function of the LV can be assessed. I.e., the mitral flow during the relaxation phase is used as an additional diagnostic marker to characterize the function of the left ventricular myocardium. One marker of impaired left ventricular diastolic function is a prolonged isovolumetric relaxation time, i.e., an increased period between aortic valve closure and mitral valve opening. Under rest conditions this time can be estimated by the period between the ventricular (paced or sensed) event and the beginning of mitral flow into the left ventricle. Another marker for diastolic malfunction is a decreased mitral flow velocity during passive filling of the left ventricle, i.e., before the atrial contraction.

The accuracy of the outlined methods based on mitral blood flow may be increased by a calibration with an external echo system. E.g., errors by a non-optimal angle of the sensor and the sound wave direction in relation to the blood stream may be compensated. Therefore, the Doppler sensor for measuring mitral blood flow is calibrated by means of an external echocardiography from time to time.

The data obtained from the sensor is condensed in IMD 10, e.g., by averaging or by data compression, and is transmitted by telemetry unit TEL 56 to a service center. Data transmission is performed in a way that is generally known from the Home Monitoring concept, e.g., by transmission from the IMD to a bedside unit and broadcasting from this device to a central service center which includes a database. In the service center the data is collected and stored on a long-term basis, evaluated, and presented to the physician. The sensor data may be input into expert systems for automatic evaluation, alarm generation on certain conditions, risk assessment etc. The data from the described acoustic sensor may be evaluated in combination with other sensor signals in the service center and information from the implant to increase the reliability of a diagnosis.

What is claimed is:

1. A heart stimulation system comprising:
    an electrode lead configured to be placed inside a coronary sinus of a heart as a coronary sinus lead comprising
        at least one stimulation electrode and
        an ultrasonic transducer configured to measure a velocity of blood flow across a mitral valve of said heart when said ultrasonic transducer is situated in the coronary sinus or a cardiac vein when in its implanted state;
    a stimulation pulse generator configured to generate electric stimulation pulses wherein said stimulation pulse generator is connected to said electrode lead that is configured to deliver said electric stimulation pulses to at least one chamber of a heart via said at least one stimulation electrode;
    memory;
    an ultrasonic transducer control unit wherein the ultrasonic transducer control unit is configured to
        excite the ultrasonic transducer with a pulse duration of approximately 1 to 5 microseconds;
        generate high frequency pulses of 3 to 9 pulses within 100 ms to 300 ms that begins with a left atrial excitation or contraction, or left atrial event and generate high frequency pulses only within a measurement period of 5 to 10 minutes a day;
        apply a time window in which to receive a reflected ultrasound signal by said ultrasonic transducer wherein the time window is arranged in chronological relation to an emission each of said high frequency ultrasonic pulses wherein said time window comprises a duration of an expected time of flight between emission of said ultrasonic pulse and a time when a reflected ultrasound signal is expected to return and
        evaluate only that part of the reflected ultrasound signal within said time window; and,
    a control unit that is connected to said memory, said stimulation pulse generator and said ultrasonic transducer via said ultrasonic transducer control unit wherein said ultrasonic transducer control unit is configured to provide a flow velocity output signal to the control unit that reflects said velocity of blood flow and wherein said control unit is configured to
        process said flow velocity output signal to optimize an atrioventricular delay AVD through measurement of said velocity of blood flow across said mitral valve after said left atrial event and
        vary the atrioventricular delay AVD for a few beats each and to determine an optimal AVD value and
        create separate tables in said memory for different event types, including atrial paced and sensed events and
        store the optimal AVD value in said separate tables based on said event types, together with the heart rate under which the optimal AVD value was determined and
        trigger right and left ventricular stimulation pulses when no intrinsic excitation of said heart occurs in a predetermined period and when said velocity of blood flow is below a threshold value with said optimal AVD obtained from said memory based on a current heart rate.

2. The heart stimulation system according to claim 1, wherein the ultrasonic transducer forms an acoustic transmitter and receiver that is implemented with a crystal comprising a sensor crystal positioned on the electrode lead.

3. The heart stimulation system according to claim 2, wherein the crystal is a piezoelectric crystal.

4. The heart stimulation system according to claim 3, wherein the piezoelectric crystal is made from Barium Titanate or Lead Zirconate Titanate.

5. The heart stimulation system according to claim 2, wherein the crystal is placed on a side of the electrode lead.

6. The heart stimulation system according to claim 2, wherein the crystal is integrated into a ring electrode that is placed on said electrode lead.

7. The heart stimulation system according to claim 1, wherein the ultrasonic transducer is configured in a way that an emitted acoustic wave travels into a direction perpendicular to the electrode lead and the reflected signal is received from that direction, respectively, wherein the ultrasonic transducer is placed on said lead at a position in the coronary sinus that is close to the mitral valve, when the electrode lead is in its implanted state.

8. The heart stimulation system according to claim 7, wherein the ultrasonic transducer is adjustable with respect to the direction an emitted acoustic wave travels along.

9. The heart stimulation system according to claim 1, wherein the ultrasonic transducer is adapted in a way that an emitted acoustic wave travels into a proximal direction with respect to the electrode lead and the reflected signal is received from that direction, respectively, wherein the ultrasonic transducer is placed on said lead at a position in a cardiac vein, when the electrode lead is in its implanted state.

10. The heart stimulation system according to claim 1, wherein the ultrasonic transducer control unit is configured to excite the ultrasonic transducer by a pulse of electrical energy within a frequency range of 2 MHz-8 MHz.

11. The heart stimulation system according to claim 10, wherein the ultrasonic transducer control unit is configured to excite the ultrasonic transducer by a pulse of electrical energy with a frequency approximately 5 MHz.

12. The heart stimulation system according to claim 10, wherein the ultrasonic transducer control unit is configured to excite the crystal with a high frequency voltage pulse having a voltage of approximately 10 volts.

13. The heart stimulation system according to claim 1, wherein the ultrasonic transducer is an ultrasound Doppler sensor.

14. The heart stimulation system according to claim 1, wherein the ultrasonic transducer has lateral dimensions that are configured to the wavelength of an emitted ultrasonic wave such that the emitted ultrasonic wave has an angle of beam spread between 10° and 60°.

15. The heart stimulation system according to claim 1, wherein the ultrasonic transducer is mounted between a matching layer in the front, a backing layer in the back and an absorbing layer behind the backing layer if viewed from outside the electrode lead.

16. The heart stimulation system according to claim 1, wherein the ultrasonic transducer is connected to the ultrasonic transducer control unit with a coax cable.

17. The heart stimulation system according to claim 1, wherein the pulse duration is shorter than an expected time of flight between emission of an acoustic wave and reception of a respective reflected signal.

18. The heart stimulation system according to claim 1, wherein the ultrasonic transducer control unit is configured to amplify and mix a received signal generated by the ultrasonic transducer after receipt of a reflected signal to eliminate a carrier frequency and to generate a Doppler shift signal that reflects said flow velocity.

19. The heart stimulation system according to claim 1, wherein the control unit is configured to repeatedly determine and store an optimal AVD value under different metabolic conditions.

* * * * *